United States Patent
Marz et al.

(10) Patent No.: US 12,178,686 B2
(45) Date of Patent: Dec. 31, 2024

(54) WET WOUND DRESSING WITH ADHESIVE EDGE

(71) Applicant: IVF HARTMANN AG, Neuhausen (CH)

(72) Inventors: Jacqueline Marz, Radolfzell (DE); Markus Rothmaier, Illnau (CH)

(73) Assignee: IVF HARTMANN AG, Neuhausen (CH)

( * ) Notice: Subject to any disclaimer, the term of this patent is extended or adjusted under 35 U.S.C. 154(b) by 683 days.

(21) Appl. No.: 17/283,415

(22) PCT Filed: Oct. 8, 2019

(86) PCT No.: PCT/EP2019/077220
§ 371 (c)(1),
(2) Date: Apr. 7, 2021

(87) PCT Pub. No.: WO2020/074512
PCT Pub. Date: Apr. 16, 2020

(65) Prior Publication Data
US 2021/0378873 A1 Dec. 9, 2021

(30) Foreign Application Priority Data
Oct. 12, 2018 (EP) ..................................... 18200151

(51) Int. Cl.
*A61F 13/0246* (2024.01)
*A61F 13/00* (2024.01)
*A61F 13/05* (2024.01)

(52) U.S. Cl.
CPC .......... *A61F 13/0253* (2013.01); *A61F 13/05* (2024.01); *A61F 2013/00582* (2013.01)

(58) Field of Classification Search
CPC ...... A61F 13/00; A61F 13/02; A61F 13/0209; A61F 13/0223; A61F 13/0246;
(Continued)

(56) References Cited

U.S. PATENT DOCUMENTS

| 5,792,089 A | 8/1998 | Penrose et al. |
| 5,947,917 A * | 9/1999 | Carte ................. A61F 13/0253 602/58 |

(Continued)

FOREIGN PATENT DOCUMENTS

| DE | 19916523 A1 | 6/2000 |
| DE | 102010020050 A1 | 11/2011 |

(Continued)

OTHER PUBLICATIONS

Eckstein, Dec. 31, 2008, Wound Dressing, Has Wound Pad Treating Wounds in Moist Medium and Provided With Planar Support Material, Which Contains Adhesive Layer Made Up of Silicone Pressure-sensitive Adhesive.*

(Continued)

*Primary Examiner* — Alireza Nia
*Assistant Examiner* — Andrew Jun-Wai Mok
(74) *Attorney, Agent, or Firm* — John Rizvi; John Rizvi, P.A. —The Patent Professor®

(57) ABSTRACT

The invention relations to a dressing (1) for treating wounds in damp or wet situations, comprising: a) a suction/rinsing body (2) which is supplied by the manufacturer with a saline aqueous solution, particularly a Ringer's solution, said solution preferably containing a substance exhibiting an antimicrobial effect, b) a planar carrier material (3) which is arranged on the side of the suction/rinsing body (2) that faces away from the wound and which projects over said suction/rinsing body (2) such that an edge extending around all sides of the suction/rinsing body (2) is formed, said edge being provided, with a layer of a skin-compatible silicone adhesive (4) on the side facing the wound, and c) a first protective layer (5) that covers the layer of a skin-compatible silicone adhesive (4) on the side facing the wound, characterized in that the wound dressing (1) comprises a (Continued)

second protective layer (6) arranged on the side of the carrier material (3) facing away from the wound, wherein both the first and the second protective layers (5,6) fully project beyond the carrier material (3), wherein the first protective layer (5) forms an opening that leaves the suction/rinsing body (2) uncovered, and wherein the first and second protective layers (5,6) protect the layer of a skin-compatible silicone adhesive (4) from contact with liquid and steam.

19 Claims, 2 Drawing Sheets

(58) Field of Classification Search
CPC ........ A61F 13/0253; A61F 2013/00021; A61F 2013/00089; A61F 2013/00255; A61F 2013/00361; A61F 2013/00634; A61F 13/05; A61L 31/146; A61M 1/90; A61M 1/91; A61M 1/96; A61M 1/912; A61M 1/913; A61M 1/915; A61M 1/916; A61M 1/917; A61M 1/918; A61M 1/962; A61M 1/964
See application file for complete search history.

(56) References Cited

U.S. PATENT DOCUMENTS

| | | | | |
|---|---|---|---|---|
| 6,008,429 | A * | 12/1999 | Ritger | A61F 13/0256 602/57 |
| 9,149,443 | B2 * | 10/2015 | Uematsu | A61K 9/7084 |
| 2008/0167631 | A1 * | 7/2008 | Greer | A61M 1/915 602/53 |
| 2014/0163485 | A1 * | 6/2014 | Knill | A61L 15/46 604/304 |
| 2017/0051189 | A1 * | 2/2017 | Tunius | A61L 31/041 |
| 2017/0128270 | A1 * | 5/2017 | Hoggarth | A61F 13/0226 |
| 2017/0189237 | A1 * | 7/2017 | Locke | A61F 13/05 |
| 2018/0030321 | A1 * | 2/2018 | Tunius | A61P 17/02 |
| 2018/0125722 | A1 * | 5/2018 | Hoggarth | A61F 13/01029 |

FOREIGN PATENT DOCUMENTS

| | | | | |
|---|---|---|---|---|
| EP | 0401949 A2 * | 12/1990 | | A61F 13/023 |
| EP | 0594034 B1 | 1/1997 | | |
| WO | WO-2006071334 A1 * | 7/2006 | | A61F 13/0203 |
| WO | WO-2007020980 A1 * | 2/2007 | | A61F 13/00029 |
| WO | WO-2009000416 A1 * | 12/2008 | | A61F 13/0203 |
| WO | 2009019229 A2 | 2/2009 | | |
| WO | 2011141454 A1 | 11/2011 | | |
| WO | 2015044532 A1 | 4/2015 | | |
| WO | 2016156619 A1 | 10/2016 | | |
| WO | 2017114825 A1 | 7/2017 | | |

OTHER PUBLICATIONS

Iwahashi, Feb. 22, 2007, Patch having easily detachable release sheet.*

International Search Report and Written Opinion from PCT/EP2019/077220 mailed Mar. 5, 2020.

* cited by examiner

WET WOUND DRESSING WITH ADHESIVE EDGE

This application claims priority to European Patent Application No. 18200151.1 filed on Oct. 12, 2018.

The present invention relates to a wound dressing for wound treatment in a moist or wet environment, comprising a suction/rinsing body treated by the manufacturer with a saline aqueous solution, and a sheetlike backing material, which is disposed on the side of the suction/rinsing body facing away from the wound and which overhangs the suction/rinsing body in such a way as to form, surrounding the suction/rinsing body on all sides, an edge which is provided, on the wound-facing side, with a layer of a skin-compatible silicone adhesive, and also to packaging for such a wound dressing, to a production method for a wound management product comprising a wound dressing in packaging, and to a kit of two or more wound dressings.

Wound dressings for wound treatment in a moist or wet environment are known from the prior art. Thus, for example, documents WO2011/141454, EP 0 594 034131 or WO2016/156619 from the applicant disclose a wound dressing of wound pad or compressed type which can be applied to a wound or can even be used for the packing of deep wounds. The suction/rinsing body is treated by the manufacturer, particularly to saturation point, with a saline aqueous solution which causes a superabsorbent material contained in the suction/rinsing body to swell and to pass into a gelatinous state. This gives the suction/rinsing body a dual function in the context of wounds exhibiting severe exudation. Wound secretions, including their critical constituents such as germs, are actively taken up by and held in the suction/rinsing body, and at the same time the suction/rinsing body delivers the saline aqueous solution to the wound and thus creates or supports a moist wound environment. As a result, wound cleansing and positive wound conditioning are supported, with a consequent positive influence on healing. This is referred to as interactive wet therapy, which is employed particularly preferably with poorly healing wounds, with clinically manifested infected wounds or with chronic wounds of differing etiology, such as diabetic gangrene, decubitus ulcers or venous ulcers.

A disadvantage of the wound dressing described in the aforesaid documents is that because of the moisture they have no inherent adhesiveness and so have to be affixed on the patient's skin necessarily by means of a secondary dressing. This problem is said to be eliminated by the provision of the wound dressing with a backing layer which at least partly overhangs the wound dressing and is provided, on the edge overhanging the wound pad, with a skin-friendly adhesive. Thus, for example, document WO2009/000416 discloses a wound dressing comprising a wound pad activated or to be activated prior to wound treatment for wound treatment in a moist environment, having a sheetlike backing material which overhangs at least in regions of the wound pad, the backing material being provided on the wound-facing side, at least in regions, with an adhesive layer for affixing the wound dressing on a substrate.

WO2017/114825 discloses a wound dressing for wound treatment particularly in a moist or wet environment, having a wound pad which can be treated by the manufacturer with a saline aqueous solution, more particularly Ringer's solution, and accommodated in surrounding packaging, the wound pad being presented by the manufacturer for delivery to the consumer in an unfolded configuration forming a plane. A feature of this wound dressing is that an adhesive edge protruding over the wound pad is folded onto the reverse side, where it is covered with a liner layer.

Particular difficulties arise here in that, on the one hand, the adhesive edge region must be protected from contact with dirt, fluid or water vapor, so that it suffers no loss of adhesion prior to application of the wound dressing. On the other hand, it must be possible for the suction/rinsing body, after production of the dry wound dressing, to be treatable with a saline aqueous solution in a manner which is advantageous from a production standpoint. The present invention as claimed in claim 1 solves these problems.

A wound dressing according to the present invention comprises a) a suction/rinsing body treated by the manufacturer with a saline aqueous solution, more particularly Ringer's solution, the solution preferably comprising a substance with antimicrobial action; b) a sheetlike backing material, which is disposed on the side of the suction/rinsing body facing away from the wound and which overhangs the suction/rinsing body in such a way as to form, surrounding the suction/rinsing body on all sides, an edge, which is provided, on the wound-facing side, with a layer of a skin-compatible silicone adhesive; and c) a first protective layer, which lines the layer of a skin-compatible silicone adhesive on the wound-facing side, wherein the wound dressing has a second protective layer, which is disposed on the side of the backing material facing away from the wound, with both the first and the second protective layers whole-sidedly overhanging the backing material, the first protective layer forming an opening which leaves the suction/rinsing body uncovered.

The aforementioned Ringer's solution is typically an aqueous solution containing sodium chloride, potassium chloride and calcium chloride (in particular, 8.6 g of NaCl, 0.3 g of KCl and 0.33 g of $CaCl_2$ per liter).

The change interval time, i.e., the usage time of a wound dressing before the next change of bandage, is supposed to be at least 24 h, with efforts made to extend the change interval time, in particular to 48 to 72 h. This would be desirable from an economic standpoint, but also for reasons of the disruption to wound healing that is caused by frequent change of bandage.

The suction/rinsing body is a wound pad which is capable of absorbing fluids. Said wound pad may consist of any material suitable for this purpose, and may comprise, for example, a foam, absorbent fibers, a textile material, a gel, or absorbent particles. In particular the wound pad is a wound pad which does not stick to the wound, comprising a shell made from a non-wound-sticking polymer material. This shell may with further preference consist of a non-wound-sticking warp-knitted, weft-knitted or woven fabric, which with further preference consists of a hydrophobic fiber material. The shell more particularly may be a warp-knitted, weft-knitted or woven fabric consisting of a hydrophobic polyethylene, polypropylene, polyester or viscose polymer material. By virtue of its embodiment as a warp-knitted, weft-knitted or woven fabric, the shell can be stretched or deformed in one or more directions without automatically contracting or adopting an orientation. The surface of a shell of this kind, moreover, conforms with an accurate fit to the surface of the skin or wound to be treated.

Preference is given to using a suction/rinsing body which comprises a mixture of absorbent fibers and superabsorbent particles and is surrounded by an envelope. On the side of the wound dressing facing away from the wound, the envelope preferably comprises a fibrous nonwoven layer, forming the outer facing side, facing away from the wound, of the wound dressing. Disposed on the wound-facing side of this fibrous nonwoven layer is a fluid-impermeable plastics film layer, and the fibrous nonwoven layer, the plastics film layer, the suction/rinsing body, and the layer of textile sheet material are not connected to one another planarly, but instead are in contact loosely and displaceably relative to one another via their planar sides. In this arrangement, the fibrous nonwoven layer, the plastics film layer, the suction/rinsing body and the layer of textile sheet material are connected to one another only along their peripheral edge, by means of a joint.

This joint between the layers, provided only on the edge side, may be formed advantageously by an ultrasonic welded joint or a laser welded joint. The ultrasonic or laser welded joint may comprise a succession of discrete ultrasonic welds. Alternatively, these ultrasonic welds may be disposed successively in an almost continuous manner such that the impression given visually is that of a continuous joint line.

The facing-side fibrous nonwoven layer mentioned may be formed of thermoplastic fiber material, more particularly of polyolefin, more particularly of polypropylene.

The basis weight of the fibrous nonwoven ply on the side of the wound dressing facing away from the wound is preferably 15-100 g/m$^2$, more preferably 20-60 g/m$^2$, very preferably 25-40 g/m$^2$.

It proves advantageous, additionally, if the density of the fibrous nonwoven layer on the side of the wound dressing facing away from the wound is 10-1000 kg/m$^3$, preferably 50-250 kg/m$^3$, more preferably 100-150 kg/m$^3$.

It proves advantageous, additionally, if the fluid-impermeable plastics film layer is formed of a thermoplastic material, more particularly of polyolefin, more particularly of polypropylene.

It proves advantageous, additionally, if the fluid-impermeable plastics film layer has a basis weight of 5-100 g/m$^2$, preferably 8-50 g/m$^2$, more preferably 10-25 g/m$^2$, and a thickness of 5-100 µm, preferably 8-50 µm, more preferably 10-25 µm.

It proves advantageous if the fibrous nonwoven-based suction/rinsing body comprises cellulosic fibers, more particularly a mixture of cellulosic fibers and thermoplastic fibers, especially polyolefin fibers, more particularly polypropylene fibers or polypropylene/polyethylene fibers.

In that case the basis weight of the fiber fraction of the suction/rinsing body is advantageously 20 to 500 g/m$^2$, preferably 30-300 g/m$^2$, more preferably 30-200 g/m$^2$, more particularly 30-150 g/m$^2$.

It proves advantageous if the density of the fiber fraction of the suction/rinsing body is 20-500 kg/m$^3$, preferably 30-300 kg/m$^3$, more preferably 50-200 kg/m$^3$. It proves advantageous, additionally, if the layer of textile sheet material is formed of a thermoplastic material, more particularly of polyolefin, more particularly of polypropylene.

It proves advantageous if the wound-facing layer composed of a textile sheet material has a coating, preferably of silicone, with a coverage of at most 70% on the wound-facing side, this coating being applied partially to the outside and in a structured manner and acting atraumatically. It proves advantageous, additionally, if the coverage of the atraumatically acting coating applied partially and in a structured manner is 20-70%, more particularly 25-50%, more particularly 30-40%.

It proves additionally advantageous if the atraumatically acting coating applied partially and in structured manner is in the form of strips. These strips may be linearly extended. They preferably run in parallel or equidistantly to one another. The width of a strip is advantageously 1 to 3 mm.

The distance of the strips from one another is advantageously 4 to 8 mm, more particularly 4 to 6 mm.

It proves advantageous, additionally, if the design of the wound dressing is such that the superabsorbent material is anionic and has negative groups and such that the aqueous solution comprises a substance with antimicrobial action, said substance comprising silver cations, biguanide or biguanide derivates, polyguanidines, N-octyl-1-[10-(4-octyliminopyridin-1-yl)decyl]pyridin-4-imine (octenidine), quaternary ammonium compounds, triazines or the ammonium compound taurolidine, and such that said substance with antimicrobial action is cationically charged at pH levels of 4-7.5 in a typical moist or wet wound environment, and is therefore attracted by negative groups of the anionic superabsorbent material and so acts antimicrobially within the suction/rinsing body. The basis weight of the superabsorbent material within the suction/rinsing body is preferably 30-150 g/m$^2$, more particularly 50-100 g/m$^2$, more particularly 60-80 g/m$^2$.

According to a further inventive concept of particular significance, it is proposed that the thickness of the wound dressing in the state treated with saline aqueous solution is 3-7 mm, more particularly 4-6 mm.

The assumption here is that the thickness of the fibrous nonwoven layer facing away from the wound, and of the plastics film layer beneath it, and also the thickness of the wound-facing layer, made of textile sheet material, with the atraumatic coating applied partially and in a structured manner, account for at most 1 mm of the overall thickness of the wound dressing moistened by the manufacturer, so that the remainder originates from the fluid-storing suction/rinsing body. Relative to existing wound dressings for wet wound therapy, the wound dressing designed as above has a significantly lower thickness. Surprisingly it has been ascertained that the absorption behavior for wound exudates is nevertheless not lowered. A possible though not yet proven explanation for this might be that a surface layer of the suction/rinsing body is responsible substantially for the absorption of wound exudate in the suction/rinsing body activated with saline aqueous solution. This inherent surprising property opens up the possibility of operating with lower basis weights of the components of the suction/rinsing body, which in turn reduces the thickness of the wound dressing overall and improves its flexibility and drapeability.

As already mentioned at the outset, the layers may be joined advantageously by ultrasonic or laser welding.

The sheetlike backing material overhangs the suction/rinsing body on all sides, to form an edge which surrounds the suction/rinsing body on all sides and which on the wound-facing side is provided with a layer of a skin-compatible silicone adhesive. A wound dressing embodied in this way is also referred to as an "island dressing".

Skin-compatible silicone adhesives which can be used include, in particular, the silicone adhesives described in K. L. Ulman, X. Thomas, "Silicone pressure sensitive adhesives for health-care applications", Advances in pressure sensitive technology-2 (1995), pp. 133-157.

As a result of the use of silicone adhesives instead of the otherwise customary adhesives used in the dressing material segment, such as natural rubber, acrylate adhesives, and also other hotmelt adhesives, the advantage is firstly that they allow the wound dressing to be affixed, with the silicone adhesives, as well as their skin-friendly characteristics, also allowing heat sterilization to take place, without the adhesive collapsing and therefore suffering a loss in its adhesiveness.

Provision here may be made for the backing material used to be a material which is heat-resistant or heat-stable in the range from 60 to 150° C. This may more particularly be a film material or a textile material, with possibilities for use as suitable base materials including polyesters, polyurethane, polypropylene or polyamide. If the base material used is polyurethane, then polyether-based or polyester-based polyurethanes may be used, with polyether-based polyurethanes having a greater thermal stability and a lower tendency to warp under the effect of heat, and therefore being preferred.

In one preferred embodiment, the backing material comprises a film material composed of polyester, polyurethane, polypropylene or polyamide that is provided with openings. The openings may have any geometric shape—for example, circular shape, oval, rectangle, square, polygon. The openings may have an effective diameter of 0.1-10 mm, preferably 1-5 mm, more preferably 1.5-3 mm. The openings may be distributed irregularly over the film area, or arranged in regular patterns. The openings may have a total open area of 1-90%, preferably of 2-75%, more preferably of 5-35%, very preferably of 10-20%. One suitable material is available under the Acrysil™ name from Zodiac (Zodiac Coating, Pusignan, France).

In an alternative preferred embodiment, the backing material comprises a textiles material which has openings. Suitable materials are described in EP2561844 or EP2561896. The material is preferably a warp-knitted or weft-knitted polyester fiber material manufactured in such a way that the meshes form very small openings with larger openings arranged between them in a regular pattern. The very small openings here have a mean diameter of less than 1.0 mm, preferably of less than 0.5 mm, more preferably of less than 0.3 mm. The larger openings have an approximately circular or oval shape and a mean diameter of 1.5 5 mm, preferably of 1.8-3.0 mm. The size selected for the meshes here is such that the very small openings are obturated with silicone adhesive during the coating operation, while the larger openings remain obturated. One suitable material is available from Zodiac under the Novespire HB™ name (Zodiac Coating, Pusignan, France).

The use of skin-friendly silicone adhesives on a backing material for the purpose of fixing a wound dressing to the skin of a patient is associated with a marked reduction in the water vapor transmission rate (MVTR) and breathability of the coated material. A sufficient water vapor transmission rate is needed, however, in order to reduce the risk of occlusion of the skin that is in contact with the layer of silicone adhesive. For this purpose it is advantageous to provide openings in the backing layer that are not obturated by the silicone adhesive. The backing material may preferably have openings which are not obturated by the applied layer of a skin-friendly silicone adhesive.

In one preferred embodiment the backing material comprises a multilayer material having at least a first layer and a second layer, with the first layer having openings which are not obturated by silicone adhesive, and the second layer being in a full-area embodiment.

The backing material may comprise a multilayer assembly of similar or different materials. In this context the backing material consists preferably of a water vapor-permeable and fluid-impermeable layer disposed on the side facing away from the wound, preferably a polyurethane layer having a thickness of 10-100 µm, preferably 15-50 µm, more preferably 20-30 µm, and of a layer provided with openings and made from a film material or textile material on the wound-facing side, being coated in turn on the wound-facing side with a skin-friendly silicone adhesive. A backing material of this kind coated with silicone adhesive preferably has a water vapor transmission rate of at least 1000 g/m²/24 h, more particularly at least 2500 g/m²/24 h, preferably at least 5000 g/m²/24 h, measured according to NF EN 13726-2 (inverted cup method).

The individual plies of the multilayer assembly may be joined to one another by any suitable method, as for example by heat, pressure, adhesive or combinations thereof.

Provision may be made here for the backing layer to have a cutout the same size as the suction/rinsing body in a central region in the layer provided with openings.

Here, the water vapor-permeable and fluid-impermeable layer disposed on the side facing away from the wound covers the suction/rinsing body on the side facing away from the wound. Preferably in this case the join between the water vapor-permeable and fluid-impermeable layer and the suction/rinsing body is mediated by an adhesive or a double-sided adhesive tape.

Provision may generally be made here for the layer of skin-friendly silicone adhesive ("adhesive layer") to be applied over the full area or else only in sections, more particularly in patterns, on the wound-facing side. As a result of application in patterns, it is possible to improve the water vapor transmission rate of the backing material in the context of an applied wound dressing of the invention. This makes it possible to counter the problem whereby the water vapor transmission rate of the wound dressing is generally lowered in the region of application of adhesive, and in particular the silicone adhesives which, while being skin-compatible, have only a limited water vapor transmission rate.

In particular, provision may advantageously be made for the adhesive layer to possess a thickness of 40 to 500 µm, preferably 100 to 450 µm, and more preferably 250 to 450 µm. With particular preference an adhesive layer thickness of 310 to 440 µm may be provided. The basis weight, being the quantity applied, is in this case preferably <375 g/m², more preferably 100-300 g/m², very preferably 150-250 g/m².

Provision may be made, furthermore, for the peel adhesion of a corresponding silicone adhesive to a substrate known as Bristol paper to correspond to at least 0.5 N/25 mm, more particularly at least 1.0 N/25 mm and very preferably at least 1.5 N/25 mm, the measurement method used here for the peel adhesion being FINAT No. 1 with a peel angle of 180° with respect to Bristol paper and a removal velocity of 300 mm per minute.

A multiplicity of shapes are conceivable, provided the wound pad is fixed on the wound dressing and affixing to a substrate can be accomplished by the backing material. It is possible here for the backing material to be provided in the form of any type of network or hole structure, the important thing being that the backing material stretches far enough over the wound pad to ensure that the wound pad is securely affixed to a wound.

Provision may be made in particular for the wound pad to be fixed on the backing material over a region of the adhesive layer, with the adhesive of the adhesive layer preferably comprising one or more silicone adhesives in this region as well. It is advantageous in this case to subject the surface of the silicone adhesive to surface activation of chemical groups before the individual parts are joined, in the region of contact between wound pad and silicone adhesive. In this case it is possible to employ chemical and/or physical methods. Suitable methods include treatments of one or both surfaces with plasma, heat, gas, liquid or corona treatment.

Particularly suitable methods are disclosed in WO2015/044532. In this way the adhesive force between wound pad and backing material is increased and the risk of delamination reduced.

Provision may be made, furthermore, for the wound-facing side of the adhesive to be provided with a protective layer which is heat-stable in the range from 60 to 150° C.

A wound dressing of the invention is a first and a second protective layer. The first protective layer covers the wound-facing side of the ply of silicone adhesive that is present on a backing layer. It protects the layer of silicone adhesive from unwanted contact with fluid, which may originate from the suction/rinsing body treated with saline aqueous solution. It also protects the layer of silicone adhesive from contact with water vapor which may occur, for example, during the sterilization process. The second protective layer covers the side of the backing material facing away from the wound, and so likewise protects the layer of silicone adhesive from unwanted contact with fluid, which may come from the suction/rinsing body treated with saline aqueous solution, and with water vapor. The first and second protective layers may more particularly comprise a film, in particular a nonswellable polymer film. Covering with a protective layer of this kind, which may also be referred to as a liner, has the advantage that the wound dressing does not stick, for example, to surrounding packaging, and hence that it is easier to remove the wound dressing from the surrounding packaging. Furthermore, both layers in unison ensure that the layer of silicone adhesive of the backing material does not make contact with fluid from the suction/rinsing body and does not make contact with water vapor.

Both the first and the second protective layer overhang the backing material whole-sidedly.

From a technical production standpoint it is advantageous in a first step first to produce a complete dry wound dressing, which subsequently in a second step is fully treated with saline aqueous solution.

Both the first protective layer and the second protective layer consist of a fluid-impermeable and water vapor-impermeable material.

This ensures that the layer of silicone adhesive of the backing material does not come into contact with fluid from the suction/rinsing body and makes just as little contact with water vapor, which is formed in large quantities particularly during the sterilization process. Contact is possible neither from the wound-facing side nor by way of the openings or the water vapor-permeable ply of the backing layer. This ensures that the layer of silicone adhesive is able to develop its undiminished peel adhesion at the start of use.

Both the first and the second layers consist of a material which is heat-stable at temperatures of 100-150° C. Suitable materials include polyester, polyamide and polypropylene. With particular preference the material of each of the first and second protective layers is a film of polyethylene terephthalate having a thickness of 40-100 μm and a basis weight of 80-100 g/m². This ensures that the protective layer retains its function at the temperatures occurring during the sterilization process.

The first protective layer contains an opening which leaves the suction/rinsing body uncovered. This ensures that the dry suction/rinsing body can be treated with saline aqueous solution in a manner which is advantageous in terms of the technical operation.

It has unexpectedly been found that it is advantageous to produce the first protective layer, second protective layer and backing layer unitarily from the same base materials. In the event of a subsequent thermal treatment, e.g., heat or steam sterilization, being carried out, the plies produced from the same base materials have identical or similar heat stabilities and coefficients of thermal expansion. If different base materials are used, different coefficients of thermal expansion may lead to creasing in the individual plies. This may have adverse consequences for the ease of application, the wear comfort and/or the security against inward penetration of dirt, fluid, gas or microorganisms.

In order to apply the wound dressing of the invention, first of all the first protective layer is removed. The remaining part of the wound dressing is applied to the wound requiring treatment. Subsequently the second protective layer is removed.

The second protective layer may have a coating of an adhesive on its wound-facing side. This results in an increased adhesive force between the backing layer and the second protective layer, which exceeds the adhesive force between the first protective layer and the layer of silicone adhesive yet is lower than the adhesive force between the patient's skin and the layer of silicone adhesive. This ensures that when the wound dressing is applied, the first protective layer is removed first and the second protective layer only subsequently, while the wound dressing remains affixed on the patient in the desired position. Accordingly, hygienic application at the desired site can be achieved.

The application of adhesive on the wound-facing side of a second protective layer may be made over the full area or partially, in strips, patterns or dots.

In an additional preferred embodiment the first protective layer is of one-part embodiment.

In one preferred embodiment the second protective layer is of two-part or multipart embodiment.

In one particularly preferred embodiment, the second protective layer has a middle region and at least one edge region, with the middle region being at least partially provided with an adhesive on the wound-facing side, and with the at least one edge region being adhesive-free. In this way a grip element is created in the edge region, which facilitates the detachment of the second protective layer from the backing material. This can be realized in a simple way by applying an additional section of material in the edge region to the adhesive-coated, wound-facing side of the second protective layer. This additional section of material may finish flush with the outside edge of the second protective layer or protrude beyond it. The additional section of material is preferably a film section made from the same material as the first and second protective layers. For ease of recognition, the additional section of material may be delimited by color. It preferably has a blue color.

In one preferred embodiment the second protective layer has at least one separating line. The at least one separating line divides the second protective layer into at least two parts. What this makes it possible to achieve is that the second protective layer can be removed from the backing layer not only from the edge, but also from the separating line. In one particularly preferred embodiment the separating line is a wavy separating line. This affords a particularly good opportunity for the user to take hold of the second protective layer and detach it from the backing layer.

In one preferred embodiment, on one side or both sides of the separating line, the region of the second protective layer that is provided with a separating line has an additional layer made of a film material, so that the sections located on one or both sides of the separating line are reinforced, so making these regions easier to take hold of. For the user, this results in better handling properties of the wound dressing as a whole. In one preferred embodiment, this region reinforced by an additional film material has a color which is different from the rest of the protective layer, being preferably blue, allowing this region to be very easily identified. Appropriate materials include polymeric films, preferably a material identical to the first and second protective layers. The additional layer of film material here may be connected via an adhesive to the side of the second protective layer facing away from the wound, so that there is no separation of the two materials with forces that occur in the course of normal use.

Provision may be made for the first protective layer on the wound-facing side and the second protective layer on the side facing away from the wound to be joined to one another via a joining element. The first protective layer in this case is joined firmly to the second protective layer at an edge side in a hingelike manner by means of the joining element. The joining element has at least two legs which are movable relative to one another. The legs of the hingelike joining element are fastened respectively on the inner or outer sides of the two first and second protective layers joined to one another. Both the first and the second protective layers have a greater areal extent than the backing layer and overhang it whole-sidedly. Both the first and the second protective layers may each have an additional shaping on the edge side opposite the joining element, this shaping serving as a grip element.

For application, the wound management product according to this embodiment is first gripped by the grip element, with one hand gripping the grip element and the other hand the part of the second protective layer overhanging the backing layer. The first protective layer is then detached from the backing layer. The first protective layer and second protective layer remain joined to one another by means of the hingelike element. The centrally disposed, moist wound pad can then be applied to a wound requiring management, and affixed, without the wound pad or the backing layer making contact with the hands. When application is complete, the second protective layer is detached from the reverse of the backing layer.

Wound dressings of the invention can be produced in any desired shape. Not only the suitable suction/rinsing bodies but also the suitable backing materials and the suitable first and second protective layers have any desired geometric shapes, such as, for example, squares, rectangles, trapeziums, triangles, pentagons, hexagons, other polygons, circles, ovals and ellipses. Preference is given to using wound dressings where not only the suction/rinsing body, but also the backing material and also the first and second protective layers have equivalent geometric shapes which differ merely in the dimensions of extent. Preference is given to square, rectangular, circular and oval wound dressings of this kind.

Surprisingly it has been ascertained that the full treatment of the dry suction/rinsing body can also be advantageously supported in a manner advantageous in processing terms by means of a particular embodiment to the packaging. A subject of the present invention is therefore also packaging for a wound dressing, with the wound dressing being a wound dressing for wound treatment in a moist or wet environment, embodied as what is called an island dressing. The wound dressing thus comprises a suction/rinsing body treated by the manufacturer with a saline aqueous solution, and a sheetlike backing material which is disposed on the side of the suction/rinsing body facing away from the wound and which overhangs the suction/rinsing body in such a way as to form, surrounding the suction/rinsing body on all sides, an edge which is provided on the wound-facing side with a layer of a skin-compatible adhesive. The wound dressing further comprises a protective layer which lines the layer of a skin-compatible adhesive on the wound-facing side. The wound dressing is preferably a wound dressing according to the invention.

Advantageous packaging for a wound dressing of this kind for wound treatment in a moist or wet environment comprises a pouch having a first pouch side composed of a first fluid-impermeable material and a second pouch side composed of a second fluid-impermeable material, which are joined to one another in a fluid-tight manner surroundingly on the edge side. The fluid-impermeable materials of the first and second pouch sides may be identical or different. They are preferably each films made of aluminum-plastic composite material, and particularly aluminum provided on the outside with a layer of polyester and on the inside with a layer of polypropylene. The first pouch side has a central region and an edge region which surrounds the central region on all sides. The central region has a depression which is shaped for positioning the wound dressing in the packaging by means of its suction/rinsing body. The shape and size of the depression are sufficient to accommodate the suction/rinsing body standing up from the wound dressing, and preferably of accommodating it fully even in the state fully treated with saline aqueous solution. The depression preferably has a shape which is complementary to the shape of the suction/rinsing body in the dry state. The depression preferably has a depth which corresponds to 50-150%, more preferably 60-140%, very preferably 80-120% and especially preferably 90-110% of the thickness of the suction-rinsing body in the dry state. The depression preferably has a longitudinal extent which corresponds to 100-300%, more preferably 100-200%, very preferably 100-150%, especially preferably 100-120% of the longitudinal extent of the suction/rinsing body in the dry state. The depression preferably has a lateral extent which corresponds to 100-300%, more preferably 100-200%, very preferably 100-150%, especially preferably 100-120% of the lateral extent of the suction/rinsing body in the dry state. The depression preferably has a shape which is complementary to the shape of the suction/rinsing body in the dry state, but whose volume is 1-200%, preferably 2-100%, more preferably 3-75% greater than the suction/rinsing body fully treated with saline aqueous solution. In preferred embodiments, the ranges disclosed here for depth, longitudinal extent, lateral extent and volume of the depression may be combined arbitrary with one another. In one particularly preferred embodiment the depression has a depth which corresponds to 90-110% of the thickness of the suction/rinsing body in the dry state, and also a longitudinal extent and lateral extent which correspond in each case to 100-120% of the longitudinal extent and lateral extent of the suction/rinsing body in the dry state. A depression of this kind can be produced for any desired pouch materials in a process known as thermoforming.

A subject of the present invention additionally is a method for producing a wound management product comprising a wound dressing of the invention and packaging of the invention. The method comprises the following steps a) providing a first pouch side composed of a first liquid-impermeable material, b) providing a depression in a central region of the first pouch side in a thermoforming process, c) filling the depression with a defined amount of saline aqueous solution preferably suitable for fully treating a suction/rinsing body of the wound dressing, d) placing a wound dressing as claimed in any of claims 1-11 onto the first pouch side, the wound dressing being positioned by means of its suction/rinsing body in the depression, e)

laying-on a second pouch side composed of a second liquid-impermeable material, f) fluid-tightly sealing the first and second pouch sides along a connecting line surrounding the entire wound dressing on all sides, and g) sterilizing.

In a production process, the first pouch side is first provided with a depression produced by thermoforming. A requisite amount of saline aqueous solution is introduced into the depression. This amount is preferably sufficient to treat the suction/rinsing body fully, in other words to saturation point, with saline aqueous solution. Subsequently a wound dressing of the invention is laid onto the first pouch side, with the wound-facing side of the wound dressing pointing in the direction of the first pouch side. The suction/rinsing body of the wound dressing here is introduced into the depression filled with saline aqueous solution on the first pouch side. The saline aqueous solution contained is absorbed fully by the suction/rinsing body. A second pouch side is subsequently located on the first pouch side in such a way that the wound dressing lying on the first pouch side is fully covered by the second pouch side. The two pouch sides are joined to one another so as to form a sealed seam which surrounds the wound dressing on all sides. On at least one side, at least a part of each of the first and second pouch sides projects beyond the sealed seam present on this side. Accordingly, these two pouch side parts overhanging the sealed seam can each be gripped by one hand and pulled apart, so that the sealed seams are opened, allowing the wound dressing located in the packaging to be removed and applied on the patient.

The wound dressing of the invention can be sterilized using a steam sterilization with opposing pressure. In this operation it is possible to use temperatures of 90-130° C.

There was no collapse of the adhesive.

Additionally a subject of the present invention is a kit for use in wound management, comprising different wound dressings. A kit of this kind comprises at least one first wound dressing of the invention and at least one second wound dressing of the invention. A kit refers to an offering two or more different wound dressings which need not necessarily be made available in joint sales units but instead, for example, in a joint offering in separate sales units. The first wound dressing here has a first suction/rinsing body having a thickness and a first geometric shape, and the second wound dressing has a suction/rinsing body having a thickness and a second geometric shape. In a kit of this kind, the thickness of the first suction/rinsing body is identical to the thickness of the second suction/rinsing body, and the first geometric shape is different from the second geometric shape. An advantage of providing a kit of wound dressings having different geometric shapes is that wound dressings suitable for different usage situations can be provided. Wound dressings in different geometric shapes have advantages, for example, in the context of application to different body sites. The provision of a kit of wound dressings having suction/rinsing bodies differing in geometric shape but identical in thickness has production advantages on the one hand, since the same starting or intermediate material for the suction/rinsing body can be used for producing wound dressings that are geometrically different in design. Furthermore, as already mentioned, the thickness of the suction/rinsing body has proven advantageous to the patient in terms of wear comfort.

A further intention is to illustrate the invention below with reference to a drawing, in which.

Figure 1:
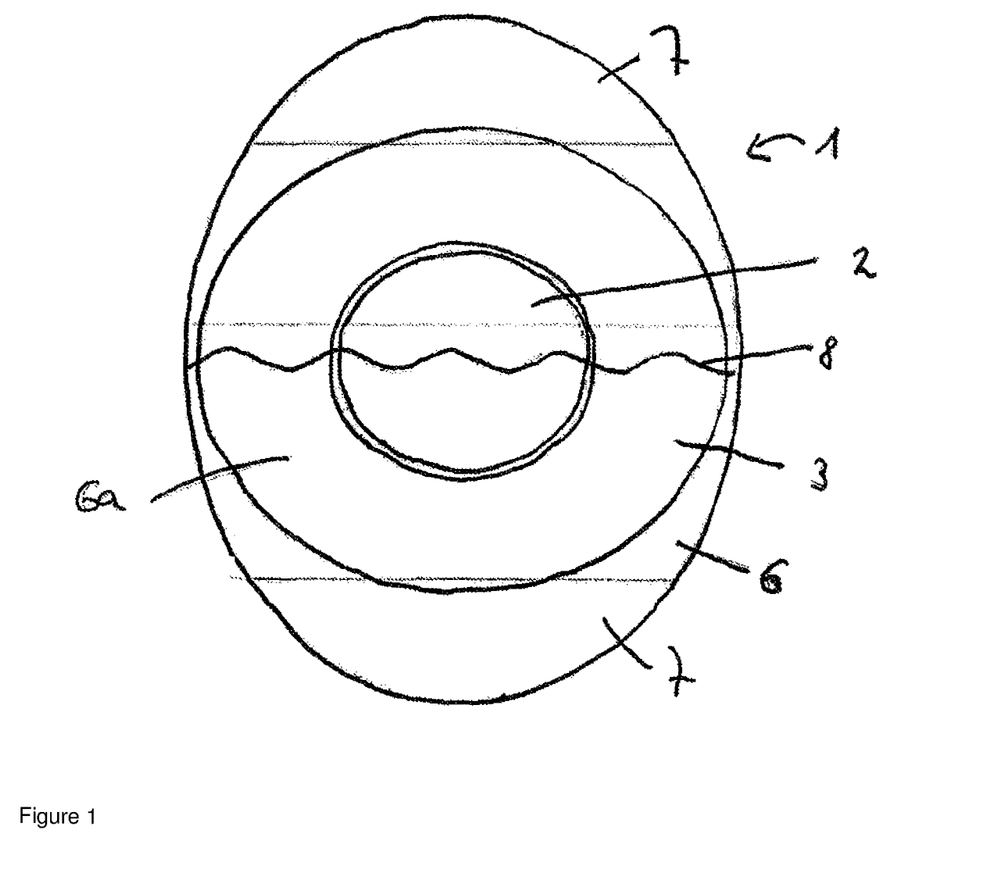
FIG. 1 shows, illustrated schematically, a wound dressing of the invention in plan view.
Figure 2:
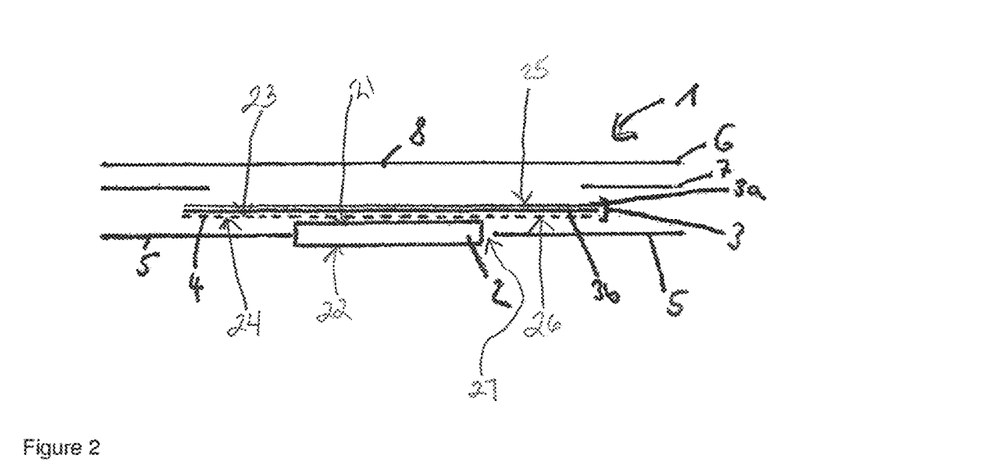
FIG. 2 shows, illustrated schematically, a wound dressing of the invention in cross section.

FIGS. 1 and 2 show a wound dressing (1) of the invention, comprising a suction/rinsing body (2) treated by the manufacturer with Ringer's solution, and a sheetlike backing material (3) on the side of the suction/rinsing body (2) facing away from the wound. The suction/rinsing body (2) has a first side 21 and a second side 22. The sheetlike backing material (3) is a two-layer material comprising a fluid-impermeable and water vapor-permeable outer layer (3a) composed of a polyurethane, and a perforated polyurethane film (3b) on the wound-facing side. The backing material (3) has a first side 25 and a second side 26. The openings in the perforated polyurethane film (3b) have an approximately circular shape. On the wound-facing side, the polyurethane film (3b) is provided with a skin-compatible silicone adhesive (4). The skin-compatible silicone adhesive (4) has a first side 23 and a second side 24. The openings in the film layer here are not obturated by the silicone adhesive.

On the wound-facing side, the wound dressing (1) has a first, one-part protective layer (5) made of polyester film in a thickness of 50 μm. There is an opening 27 of the first protective layer (5). The first protective layer (5) has a first end 30 and a second end 31.

On the side facing away from the wound, the wound dressing (1) has a second protective layer (6), coated over its full area with an acrylate adhesive. The second protective layer (6) has a first end 28 and a second end 29. The second protective layer has grip elements/projections configured for gripping (7) at two edges. These grip elements (7) are formed of sections of material composed of polyethylene terephthalate, which are applied on the wound-facing side of the second protective layer (6) and are joined to the second protective layer (6) via the acrylate adhesive. The grip elements (7) are set off in terms of color from the second protective layer (6). The second protective layer (6) is separated in the middle into two parts by means of a serpentine separating line (8).

Figure 3:
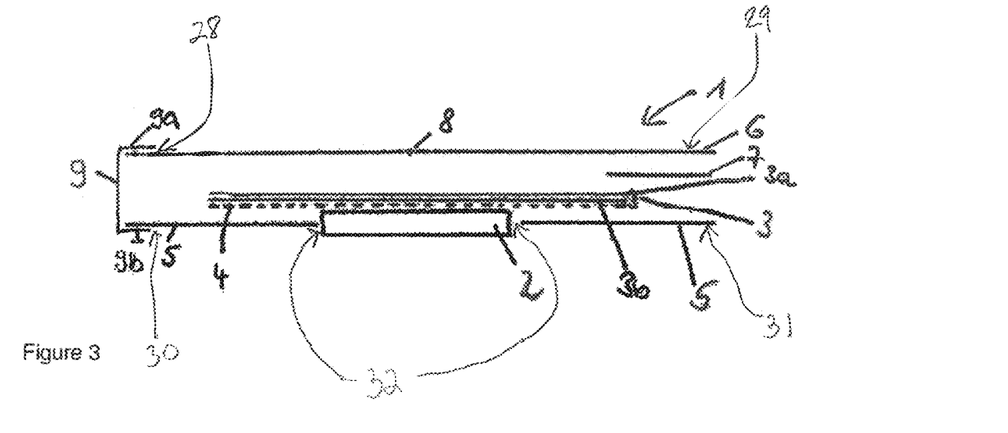
FIG. 3 shows, illustrated schematically, a wound dressing of the invention in an alternative embodiment in cross section.

FIG. 3 shows a wound dressing of the invention as a further embodiment of the wound dressing described in FIG. 2. In this embodiment, the first and second protective layers (5, 6) are joined firmly to one another in a hingelike manner by means of a connecting element (9) at one edge side, with the legs (9a, 9b) of the hingelike connecting element (9) being fastened respectively on the outer sides of the two first and second protective layers (5,6) joined to one another. FIG. 3 shows the circumferential wall 32 on either side of suction/rinsing body (2).

Figure 4:
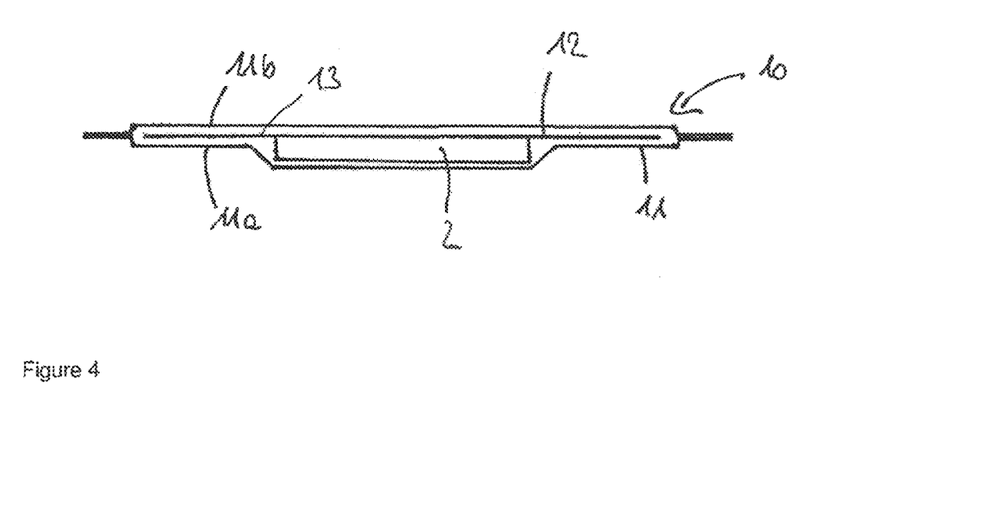
FIG. 4 shows packaging, illustrated schematically, for a wound dressing of the invention in cross section.

FIG. 4 shows packaging (10) of the invention with a wound dressing (12). The wound dressing is a wound dressing (12) for wound treatment in a moist or wet environment, embodied as what is called an island dressing. The wound dressing (12) comprises a) a suction/rinsing body (2), treated by the manufacturer with a saline aqueous solution, b) a sheetlike backing material (3), which is disposed on the side of the suction/rinsing body (2) facing away from the wound and which overhangs the suction/rinsing body (2) in such a way as to form, surrounding the suction/rinsing body (2) on all sides, an edge which on the wound-facing side is provided with a layer of a skin-compatible adhesive, and c) a protective layer which lines the layer of the skin-compatible adhesive on the wound-facing side. The packaging is formed by a pouch (11) composed of a first section (11*a*) of material and a second section (11*b*) of material. The first and second sections of material are each films made of aluminum coated on the outside with polyester and on the inside with polypropylene. The first section (11*a*) of material has a depression, the shape of which is complementary to that of the suction/rinsing body (2) and the size of which is suitable for accommodating a suction/rinsing body (2) of a wound dressing (12) contained.

The invention claimed is:

1. A wound dressing comprising:
a suction body comprising opposite first and second sides, the suction body being treated with a saline solution;
an adhesive layer comprising opposite first and second sides, the second side of the adhesive layer directly engaging the first side of the suction body;
a backing material comprising opposite first and second sides, the second side of the backing material directly engaging the first side of the adhesive layer;
a first protective layer facing the second side of the adhesive layer and positioned such that the second side of the suction body extends through an opening of the first protective layer; and
a second protective layer facing the first side of the backing material and,
wherein the suction body includes a circumferential wall extending from the first side of the suction body to the second side of the suction body, the suction body extending through the opening of the first protective layer such that the first protective layer directly engages opposite portions of the circumferential wall.

2. The wound dressing recited in claim 1, wherein the first and second protective layers each include opposite first and second ends, the first ends being hinged coupled to one another.

3. The wound dressing recited in claim 2, wherein the second ends are not connected to one another.

4. The wound dressing recited in claim 1, wherein the first and second protective layers each include opposite first and second ends, the first ends being hinged coupled to one another by a connector, the connector having a first leg that engages an outer surface of the first protective layer and a second leg that engages an outer surface of the second protective layer that faces opposite the outer surface of the first protective layer.

5. The wound dressing recited in claim 4, wherein the legs each extend parallel to the backing material.

6. The wound dressing recited in claim 1, wherein the second protective layer includes a first section and a second section that is separated from the first section by a slit.

7. The wound dressing recited in claim 6, wherein the slit has a serpentine configuration.

8. The wound dressing recited in claim 6, wherein the slit is positioned over the backing material.

9. The wound dressing recited in claim 1, wherein the wound dressing comprises projections extending from two edges of the second protective layer, the projections being configured for gripping.

10. The wound dressing recited in claim 9, wherein the second protective layer includes a first color and the projections each include a second color that is different than the first color.

11. The wound dressing recited in claim 1, wherein the backing material surrounds the suction body on all sides.

12. The wound dressing recited in claim 1, wherein the adhesive layer surrounds the suction body on all sides.

13. The wound dressing recited in claim 1, wherein the adhesive layer comprises silicone adhesive.

14. The wound dressing recited in claim 1, wherein the backing material is a sheet.

15. The wound dressing recited in claim 1, wherein the backing material is a polymeric film.

16. The wound dressing recited in claim 1, wherein the backing material is a textile material.

17. The wound dressing recited in claim 1, wherein the backing material comprises a first layer that is coupled directly to the first side of the suction body and a second layer that is coupled directly to an adhesive coated on the second protective layer on the side facing the backing material.

18. A wound dressing comprising:
a suction body comprising opposite first and second sides, the suction body being treated with a saline solution;
an adhesive layer comprising opposite first and second sides, the second side of the adhesive layer directly engaging the first side of the suction body;
a backing material comprising opposite first and second sides, the second side of the backing material directly engaging the first side of the adhesive layer;
a first protective layer facing the second side of the adhesive layer and positioned such that the second side of the suction body extends through an opening of the first protective layer; and
a second protective layer facing the first side of the backing material,
wherein the first and second protective layers each include opposite first and second ends, the first ends being hinged coupled to one another by a connector, the connector having a first leg that engages an outer surface of the first protective layer and a second leg that engages an outer surface of the second protective layer that faces opposite the outer surface of the first protective layer, the legs each extending parallel to the backing material,
wherein the second protective layer includes a first section and a second section that is separated from the first section by a slit having a serpentine configuration, the slit being positioned over the backing material,
wherein the adhesive layer comprises silicone adhesive,
wherein the backing material is a sheet,
wherein the backing material comprises a first layer that is coupled directly to the first side of the suction body and a second layer that is coupled directly to an adhesive coated on the second protective layer on the side facing the backing material,
wherein the suction body includes a circumferential wall extending from the first side of the suction body to the second side of the suction body, the suction body extending through the opening of the first protective layer such that the first protective layer directly engages opposite portions of the circumferential wall,
wherein the wound dressing comprises projections extending from two edges of the second protective layer, the projections being configured for gripping, and
wherein the second protective layer includes a first color and the projections each include a second color that is different than the first color.

19. A wound dressing consisting of:
a suction body comprising opposite first and second sides, the suction body being treated with a saline solution;

an adhesive layer comprising opposite first and second sides, the second side of the adhesive layer directly engaging the first side of the suction body;

a backing material comprising opposite first and second sides, the second side of the backing material directly engaging the first side of the adhesive layer;

a first protective layer facing the second side of the adhesive layer and positioned such that the second side of the suction body extends through an opening of the first protective layer; and a second protective layer facing the first side of the backing material, wherein the first and second protective layers each include opposite first and second ends, the first ends being hinged coupled to one another by a connector, the connector having a first leg that engages an outer surface of the first protective layer and a second leg that engages an outer surface of the second protective layer that faces opposite the outer surface of the first protective layer, the legs each extending parallel to the backing material, wherein the second protective layer includes a first section and a second section that is separated from the first section by a slit having a serpentine configuration, the slit being positioned over the backing material, wherein the adhesive layer comprises silicone adhesive, wherein the backing material is a sheet, wherein the backing material comprises a first layer that is coupled directly to the first side of the suction body and a second layer that is coupled directly to an adhesive coated on the second protective layer on the side facing the backing material, wherein the suction body includes a circumferential wall extending from the first side of the suction body to the second side of the suction body, the suction body extending through the opening of the first protective layer such that the first protective layer directly engages opposite portions of the circumferential wall, wherein the wound dressing comprises projections extending from two edges of the second protective layer, the projections being configured for gripping, and wherein the second protective layer includes a first color and the projections each include a second color that is different than the first color.

* * * * *